US008281500B2

(12) United States Patent
Hedberg et al.

(10) Patent No.: US 8,281,500 B2
(45) Date of Patent: Oct. 9, 2012

(54) DEVICE AND METHOD FOR INCREASING EVAPORATION RATES OF BLOW-DOWN APPARATUS

(75) Inventors: Herbert J. Hedberg, N. Attleboro, MA (US); Brian A. Kangas, Millbury, MA (US); Michael A. Burns, West Greenwich, RI (US)

(73) Assignee: Modular SFC, LLC, Franklin, MA (US)

( * ) Notice: Subject to any disclaimer, the term of this patent is extended or adjusted under 35 U.S.C. 154(b) by 360 days.

(21) Appl. No.: 12/605,655

(22) Filed: Oct. 26, 2009

(65) Prior Publication Data

US 2010/0101109 A1 Apr. 29, 2010

Related U.S. Application Data

(60) Provisional application No. 61/108,162, filed on Oct. 24, 2008.

(51) Int. Cl.
*B01D 1/14* (2006.01)
*B01D 3/00* (2006.01)

(52) U.S. Cl. ............................ 34/181; 34/231; 159/16.1

(58) Field of Classification Search .................... 34/487, 34/507, 179, 181, 218, 229, 231; 159/16.1
See application file for complete search history.

(56) References Cited

U.S. PATENT DOCUMENTS

| | | | | |
|---|---|---|---|---|
| 2,290,323 | A | 7/1942 | Graham | |
| 2,542,681 | A * | 2/1951 | Kinney et al. | 261/95 |
| 3,031,174 | A | 4/1962 | Swanton | |
| 3,457,982 | A * | 7/1969 | Sephton | 159/13.2 |
| 4,600,473 | A | 7/1986 | Friswell | |

FOREIGN PATENT DOCUMENTS

| | | | |
|---|---|---|---|
| WO | WO 00/13761 | A1 | 3/2000 |
| WO | WO 2009/123766 | A1 | 10/2009 |

OTHER PUBLICATIONS

U.S. Appl. No. 61/108,162, filed Oct. 24, 2008, Hedberg et al.
"Notification of Transmittal of the International Search Report and the Written Opinion of the International Searching Authority, or the Declaration", International Application No. PCT/US2009/005806, filed Oct. 26, 2010, mailed Feb. 3, 2010, 14 pages.

* cited by examiner

*Primary Examiner* — Jiping Lu
(74) *Attorney, Agent, or Firm* — Cesari and McKenna, LLP; John F. McKenna

(57) ABSTRACT

A drying container insert that manages the evaporation rate of liquid solutions when subjected to blow-down gas flows. Certain gas flow separator baffles or framed inserts with vanes may be especially effective to enhance evaporation when combined with aggressive blow-down flow rates and centrifugal force. The centrifugal force applied to the evaporating liquid protects sample integrity by preventing the solution(s) from splashing out of the drying container. Such splashing, when high blow-down gas flow rates are directed into the sample containers, affects yield and purity.

6 Claims, 4 Drawing Sheets

DEVICE AND METHOD FOR INCREASING EVAPORATION RATES OF BLOW-DOWN APPARATUS

CROSS-REFERENCE TO RELATED APPLICATIONS

The present application claims the benefit of U.S. Provisional Patent Application Ser. No. 61/108,162, which was filed on Oct. 24, 2008. This provisional application is of common inventorship and ownership, and is hereby incorporated herein by reference.

BACKGROUND OF THE INVENTION

1. Field of the Invention

The present disclosure relates to an apparatus and a method for increasing evaporation rates of solutions within sample containers subjected to a drying gas flowing into the sample container.

2. Background Information

Sample concentrators are prevalent in processing liquid solutions containing a sample material or materials of interest. Materials of interest are typically synthesized, modified, and purified, in solution-based process steps. To recover these dissolved non-volatile materials as dry powders, or to increase the concentration of compounds, vacuum centrifuges, freeze drying, and blow down concentrators are commonly used.

Vacuum concentrators and freeze dryers generally require a powerful vacuum pump to produce the low levels of ambient pressure necessary to promote the ejection and escape of solvent molecules from the surface of the solution. These solvent molecules migrate to the lower concentration region of a cold trap solvent collection container and condense into liquid and/or freeze into ice.

Blow-down concentrators generally create a continuous flow of a small amount of gas onto the surface of the liquid solution. The gas flow may promote the escape of solvent molecules from the solution container that are then carried away in the flow of gas out an exhaust port. Flow rates may be typically 1 or 2 liters/minute to prevent loss of solution or dry compound from the sample container.

FIG. 1 illustrates a jet of blow-down gas directed 2 into half of the opening of a conventional test tube containing liquid 8 to be evaporated. Because the neck of the tube directs the incoming and exiting streams of gas into the same region, turbulent interaction 4 occurs, and the gas exits 6 without nearing the surface 10 of the liquid 8. A laminar high volume flow of blow-down gas striking the surface 10 of the liquid is the goal, but it may not be achieved due to the turbulence. In FIG. 1, the liquid surface is vertical, as the test tube is being depicted in an operating centrifuge meant to retain the liquid and sample within the container.

SUMMARY OF THE INVENTION

The present application discloses an insert for a liquid holding container. The insert includes a frame sized to fit snugly but smoothly into an opening into and along at least part of the length of the container. The top end of the frame includes a top vane that is wider than the container opening, so that the insert, when inserted into the container, comes to rest with the top vane resting on the container opening. Vanes are spaced apart and attached along the frame and extend, at least partially, from one side to the opposite side of an internal width of the container and are distributed along the length of the frame at a tilt angle and a pitch angle. The pitch enables a first passage for the incoming gas to flow in a laminar fashion through and reach the surface of a liquid held in the container and then to return via a second passage on the other side of the frame and exit via the container opening. The tilt angle prevents a vane that might be partially immersed in the liquid from fully blocking the path connecting the first and the second passages.

In some applications, the user may desire to have some amount of the liquid remain in the container. In those applications an end of stop vane may be positioned along the frame to block the path that connected the first and the second passages.

In some application, the frame may comprise two parallel rails that fit snugly along opposing inner sides of a container.

Other applications may use a single rail that extends down the center of the container with vanes extending to opposing inner sides of the container and fixed along the rail at a tilt angle and a pitch angle. In one example, the angles might be 20 degrees.

BRIEF DESCRIPTION OF THE DRAWINGS

The invention description below refers to the accompanying drawings, of which:

FIG. 7 through FIG. 11 illustrate the insert of FIG. 3 as the level of liquid in a test tube changes.

DETAILED DESCRIPTION OF AN ILLUSTRATIVE EMBODIMENT

Figure 1:
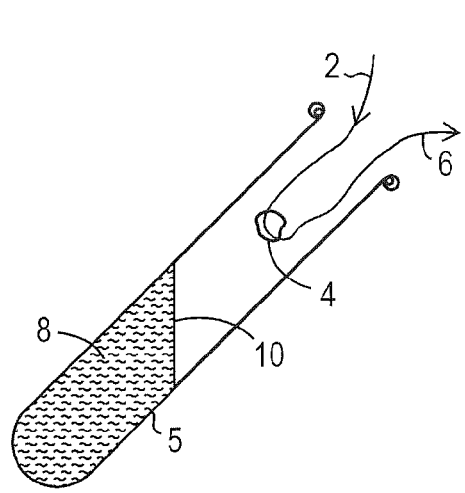
FIG. 1 already described, illustrates a limitation of a conventional test tube used for blow-down drying.
Figure 2:
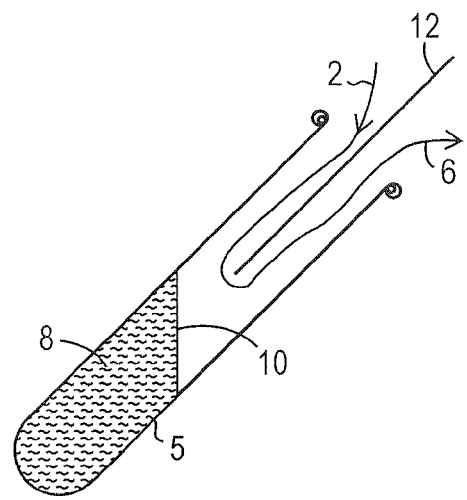
FIG. 2 is a drawing illustrating an approach to the limitation of FIG. 1.

FIG. 2 shows a baffle 12 inserted into the test tube 5. Here the incoming gas is directed 2 down to the liquid surface 10 and back out 6 on the other side of the baffle 12 without the turbulence of FIG. 1. However, as the liquid 8 evaporates and is carried away by the exiting gas 6, the surface 10 retreats from the end of the baffle 12 and the turbulence returns at the end of the baffle.

Figure 3:
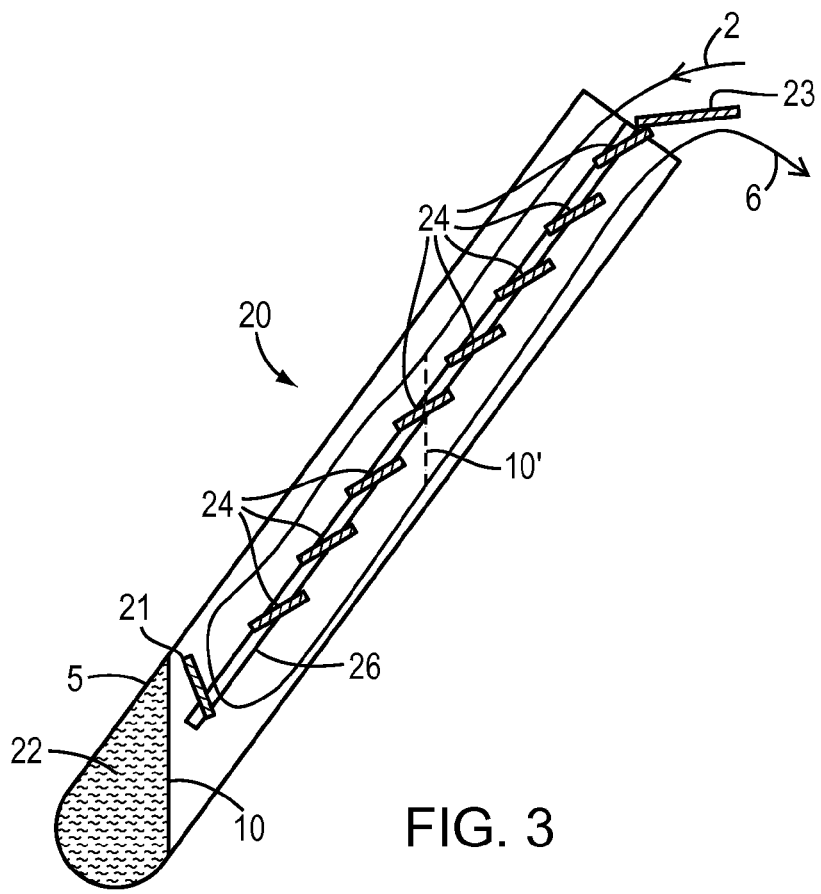
FIG. 3 illustrates another approach to the limitation of FIG. 1.

FIG. 3 illustrates an insert 20 accordingly to the invention which may extend to the bottom of the test tube 5. But in FIG. 3, the insert ends with a stopping vane 21 located before the bottom. The stopping vane prevents the drying gas flow 2 from reaching the liquid surface 10 when only a small amount of liquid 22 remains at the bottom of the test tube. The top vane 23 is wider than the test tube opening and so rests on the test tube and defines how far the insert may extend into the test tube. The top vane 23 is angled to divert the exiting gas 6 away from the entering gas 2.

The insert 20 has a frame 26 having two parallel rails that extend into the test tube close to the test tube's opposing inner walls. Other vanes 24 connect to each rail and hold the rails near the opposing inner walls.

The vanes 24 are angled with respect to the center axis of the test tube and the plane defined by the frame rails. The angle is heuristically determined to accommodate the laminar incoming gas flow 2 to reach the surface 10 before the liquid surface reaches the stopping vane 21. The laminar flow then strikes the liquid surface 10, picks up solvent molecules, and exits via the flow path 6.

Figure 4:
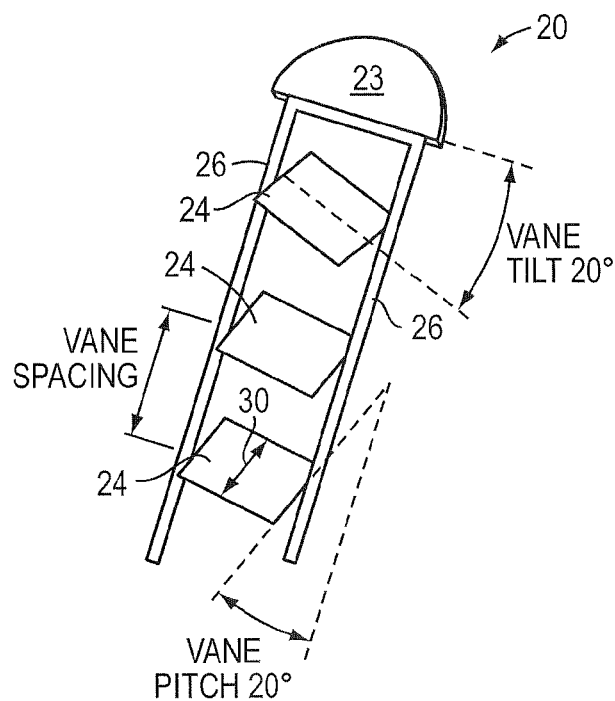
FIG. 4 is a drawing of an insert that is directed to the limitation of FIG. 1.

FIG. 4 illustrates the insert 20 without the stopping vane 21 of FIG. 3. The top vane 23, as mentioned just above, is wider that the test tube opening and it rests on the opening of the test tube. The vane 23 is angled with respect to the axis of the test tube to divert the existing gas away from the entering gas. The two parallel rails of frame 26 smoothly run adjacent to the inner walls of the test tube as they extend from the top vane into the test tube. Vanes 24 bridge between the two rails. The vanes are set at an angle, vane tilt, with respect to the rails of about 20° from normal to the rails. In addition the vanes have a pitch of 20° with respect to the plane defined by the two rails. The vanes are spaced apart by 0.635 cm and have a width 30 of about 0.200 cm.

Figure 5:
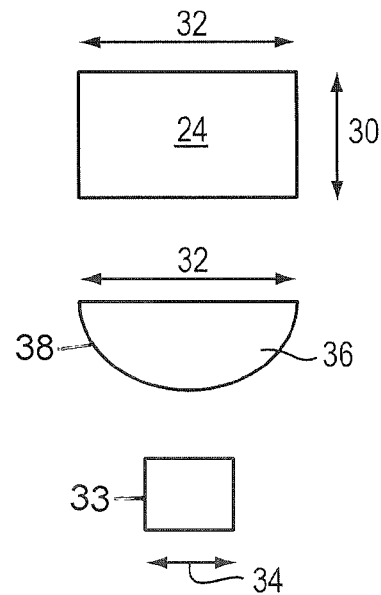
FIG. 5 is a detail of the drawing in FIG. 4.

FIG. 5 illustrates vanes of several different dimensions that may be employed. Vane 24 is rectangular with a width 30 of 0.200 cm and a length 32 that bridges the spacing of the rails 26. Vane 36 also has a length 32 and presents a curved profile 38 and vane 33 presents a vane length 34 that only partially bridges the spacing between the rails. These are examples, as other shapes may be heuristically found to be advantageous.

Figure 6:
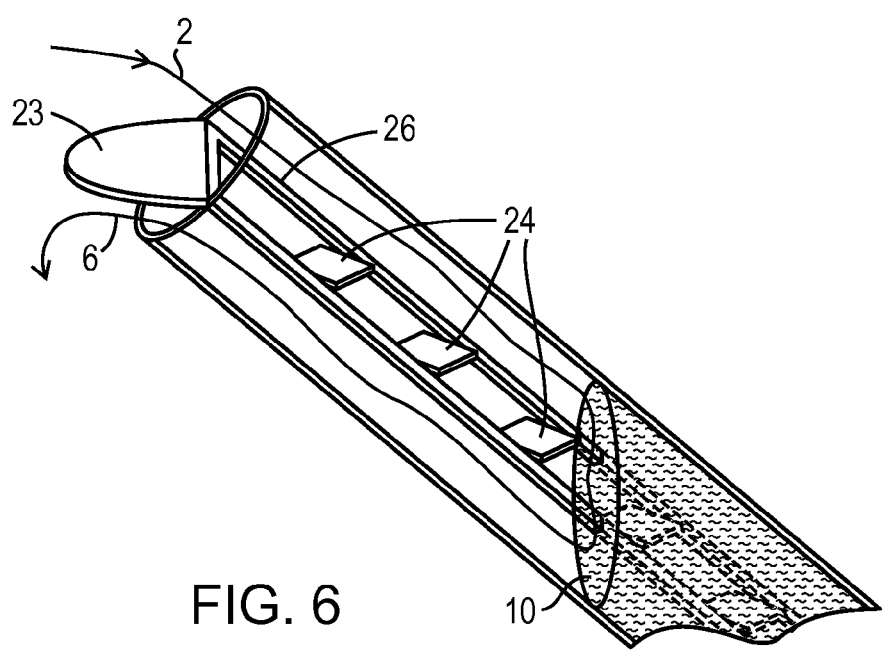
FIG. 6 is a detail of the drawing in FIG. 4.
Figure 7:
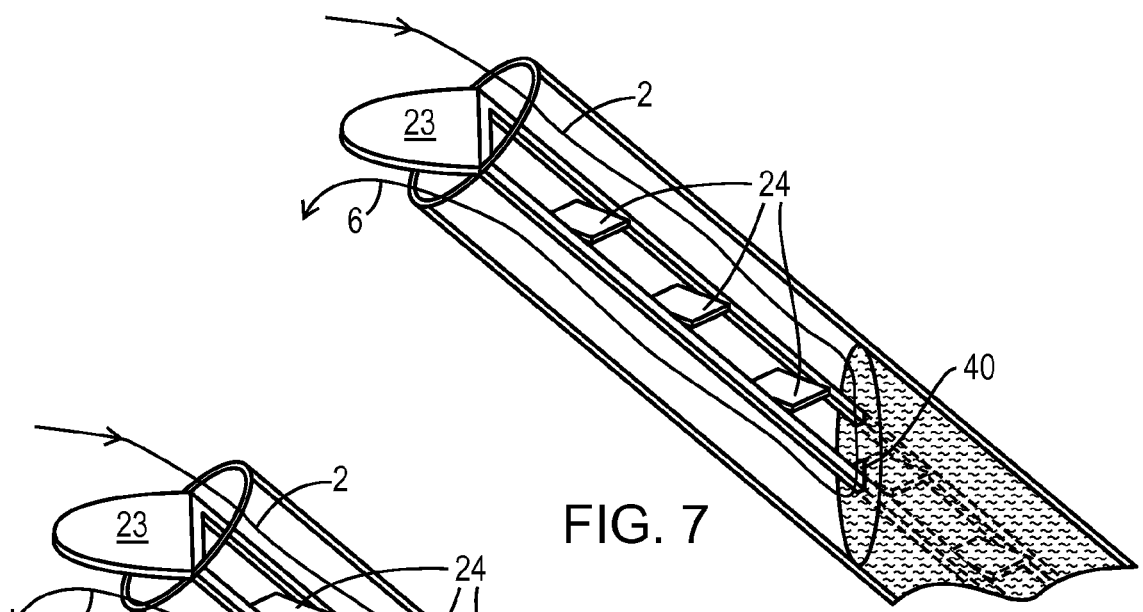
Figure 8:
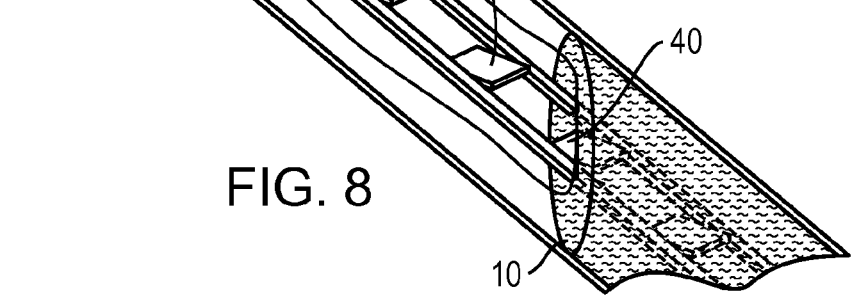
Figure 9:
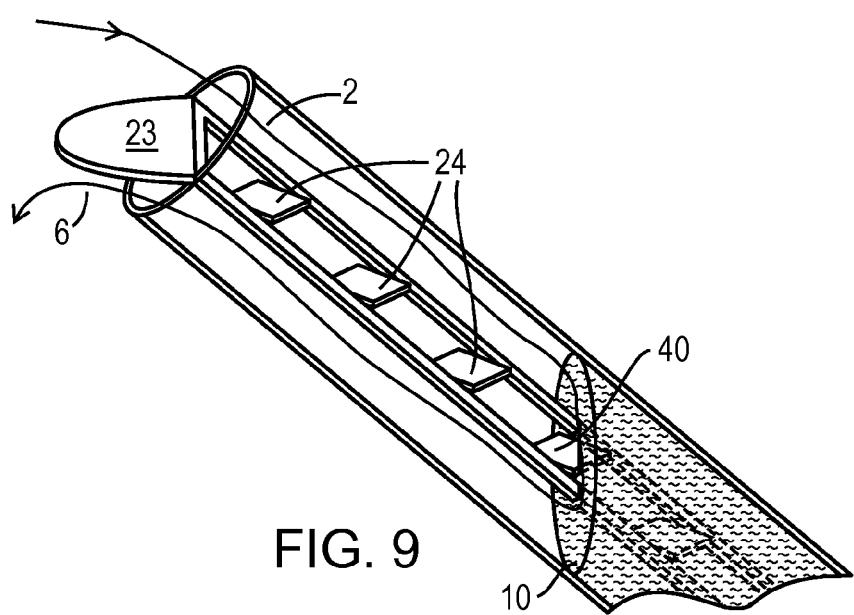
Figure 10:
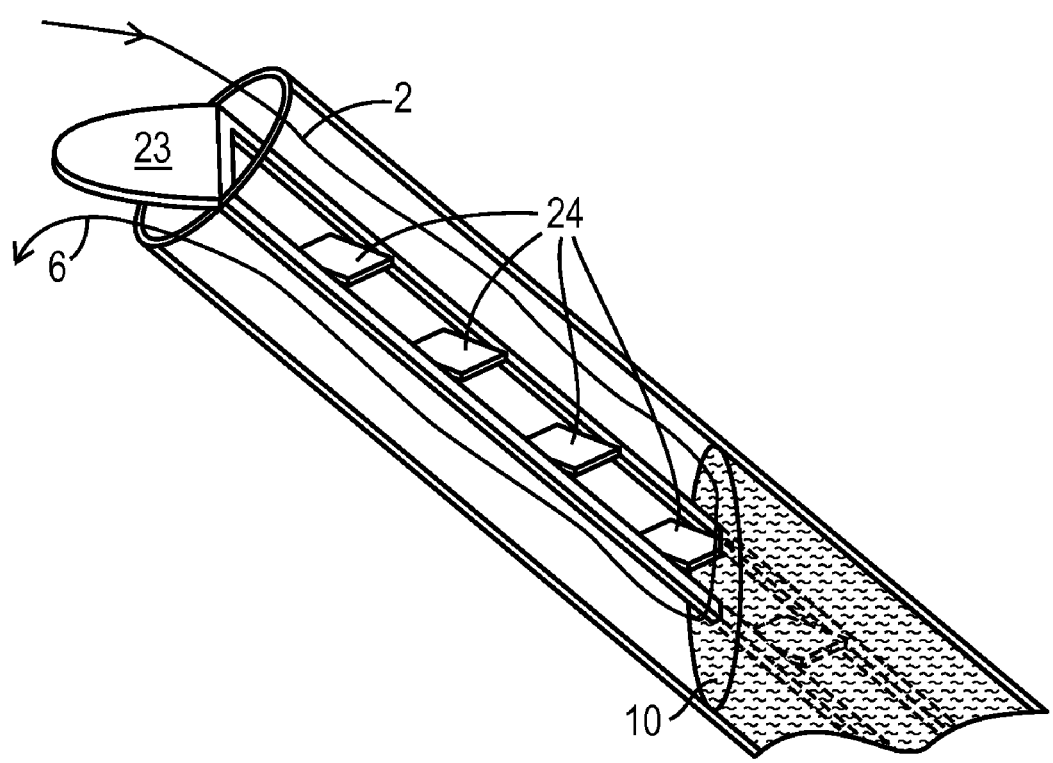

FIG. 6 illustrates the gas flow 2 flowing to the liquid surface 10 and back out 6. In this case, the surface 10 does not intersect with a vane and the entire liquid surface 10 subjected to the gas flow 2. FIG. 7 shows the liquid surface 10 intersecting with a corner 40 of a vane. The intersection is with a corner of the vane since the vanes are tilted. FIGS. 8 through 11 show the progression of the corner 40 as it emerges from the liquid surface 10. Notice that in FIG. 9, half of the vane surface interferes with the gas flow 2 and 6, but that the vane surface does not occlude the gas flow path from striking the liquid surface. FIGS. 10 and 11 show the vane 24 fully emerged from the liquid surface.

There is relatively little constraint on the particular form factor of the standard collection container. Common container types would include 0.6 mL and 1.6 mL micro-centrifuge tubes, 2 dram (1.8 mL) and 4 dram (4 mL) sample injection vials, and 20 mL and 40 mL scintillation vials. An insert may be made for virtually any container type or size.

It should be understood that the above described embodiments are being presented herein as examples and that many variations and alternatives thereof are possible. Accordingly, the present invention should be viewed broadly as being defined only as set forth in the hereinafter appended claims.

What is claimed is:

1. An insert for a container for holding a liquid, the insert comprising:
    a frame sized to fit snugly but smoothly into an opening into and along at least part of the length of the container, the frame having first and second ends;
    a top vane at the first end of the frame, the top vane having a width wider than the container opening, so that the insert, when inserted into the container, comes to rest with the top vane adjacent to the container opening;
    a stopping vane at the second end of the frame;
    additional vanes spaced apart and attached to the frame, the additional vanes extending from one side to the opposite side of an internal width of the container, said additional vanes being distributed along the length of the frame at a selected tilt angle and a selected pitch angle, wherein a gas may enter the container opening and, due to the additional vanes and their distribution, flow along one side of the frame and pass over the surface of a liquid in the container and, carrying some of the liquid molecules, exit the container along the other side of the frame, said stopping vane blocking the flowing gas from reaching beyond the stopping vane.

2. The insert of claim 1 wherein the flowing gas travels in a laminar manner along both sides of the frame.

3. The insert of claim 1 wherein the additional vanes are positioned across a portion of the width of the container while defining an entrance passage for the flowing gas to reach toward any liquid in the container, and wherein the additional vanes define an exit passage for the flowing gas, wherein mixing of the entering gas and the exiting gas is substantially eliminated.

4. The insert of claim 1 wherein the tilt and the pitch of the additional vanes are both about 20 degrees, the spacing between the additional vanes is about 0.635 cm and the vane width is about 0.20 cm.

5. The insert of claim 1 wherein the frame comprises two opposing rails that extend longitudinally into the container, the vanes bridge the two rails, and the vanes are flat panels.

6. An insert for a container for holding a liquid, the insert comprising:
    a frame sized to fit snugly but smoothly into an opening into and along at least part of the length of the container, the frame having first and second ends;
    a top vane at the first end of the frame, the top vane having a width wider than the container opening, so that the insert, when inserted into the container, comes to rest with the top vane adjacent to the container opening;
    additional vanes spaced apart and attached to the frame, the additional vanes extending from one side to the opposite side of an internal width of the container, said additional vanes being distributed along the length of the frame, each oriented at a selected tilt angle and a selected pitch angle, and all of said additional vanes being tilted and pitched in the same directions relative to the frame wherein they define a gas flow path which follows a substantially straight course along one side of the frame, passes over the surface of a liquid in the container, follows a substantially straight course along the other side of the frame and exits the container.

* * * * *